United States Patent [19]

Enqvist

[11] Patent Number: 4,514,297
[45] Date of Patent: Apr. 30, 1985

[54] BIOREACTOR

[75] Inventor: Johan R. Enqvist, Kauniainen, Finland

[73] Assignee: A. Ahlstrom Osakeyhtio, Noormarkku, Finland

[21] Appl. No.: 558,931

[22] Filed: Dec. 7, 1983

[30] Foreign Application Priority Data

Dec. 9, 1982 [FI] Finland ................ 824229

[51] Int. Cl.$^3$ .............. C12M 1/06; C12M 1/02; C02F 3/28
[52] U.S. Cl. .................. 210/194; 210/197; 210/603; 48/111; 435/314; 435/316; 435/801; 435/813
[58] Field of Search .............. 210/178, 179, 180, 188, 210/194, 195.3, 603, 197; 48/111, 197 A; 422/227, 229, 233, 184; 435/314, 316, 801, 813

[56] References Cited

U.S. PATENT DOCUMENTS

| 2,134,571 | 10/1938 | Morlock | 422/227 |
| 3,487,017 | 12/1969 | Thorn et al. | 210/197 |
| 3,493,494 | 2/1970 | Knibb | 210/180 |
| 3,607,121 | 9/1971 | Watson et al. | 422/223 |
| 4,255,389 | 4/1981 | Jung et al. | 422/233 |

FOREIGN PATENT DOCUMENTS 316767 12/1956 Switzerland ................ 210/180
2037731 10/1982 United Kingdom .

Primary Examiner—Benoît Castel
Attorney, Agent, or Firm—Bucknam and Archer

[57] ABSTRACT

A reactor for the anaerobic digestion of organic sludge and for the production of methane gas, comprises an essentially horizontal cylindrical vessel provided with an agitator rotating around an essentially horizontal shaft, an inlet for introducing the sludge to be digested at one end of said vessel, at its opposite end an outlet for removing the digested matter from the vessel and in the upper portion of the vessel an outlet/outlets for the recovery of methane gas. For returning the solids settled on the bottom of the vessel from the outlet end of the vessel to the inlet end of the vessel, the vessel comprises a channel connecting the outlet end of the vessel with the inlet end of the vessel and a device for guiding the solids to the front of the return channel and for their transport through the return channel by means of gas.

2 Claims, 3 Drawing Figures

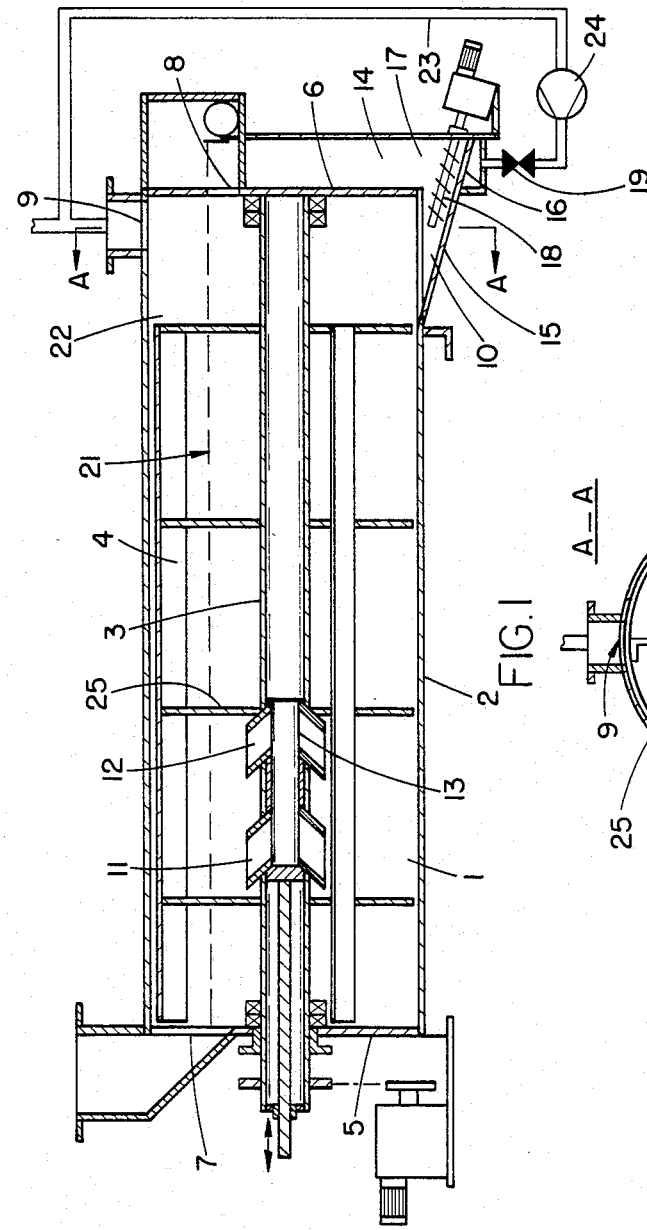
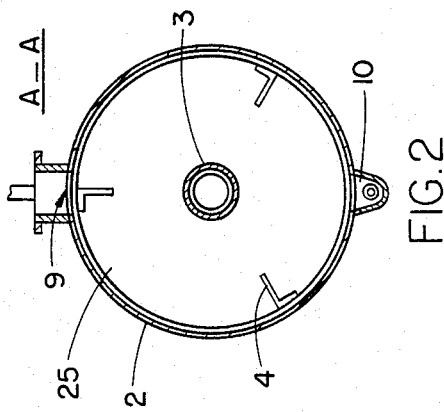
FIG.1
FIG.2

BIOREACTOR

FIELD OF INVENTION

This invention relates to a reactor for the anaerobic digestion of organic sludge and for the production of methane gas, which comprises an essentially horizontal cylindrical vessel provided with an agitator rotating around an essentially horizontal shaft, an inlet channel for introducing the sludge to be digested at one end of said vessel, at its opposite end an outlet channel for removing the digested matter from the vessel and in the upper portion of the vessel an outlet pipe for the recovery of methane gas. The vessel comprises a device for returning the solids settled on the bottom of the vessel from the outlet end of the vessel to the inlet end of the vessel.

BACKGROUND OF THE INVENTION

British patent specification No. 2,037,731 discloses a reactor provided with an agitator which is rotated around a horizontal shaft and in which the recycling of the solids settled on the bottom of the vessel from the outlet end of the reactor to the inlet end is performed by means of a pipe rotating together with the agitator and forming an angle with the shaft. The disadvantage of this known solution is that the amount of the recycled solids cannot be adjusted. The return pipe may be clogged and then the entire reactor has to be opened and emptied.

SUMMARY OF THE INVENION

The main object of the present invention is to prevent the above disadvantages.

A bioreactor according to the invention is mainly characterized in that the recycling apparatus comprises a channel connecting the outlet end and the inlet end of the vessel and means for guiding the solids settled on the bottom of the vessel to the return channel and transferring them by means of gas through the return channel. A gas produced in the reactor is preferably used as the transfer gas.

The most important advantages of the solution according to the present invention in addition to the adjustablility are as follows:

the solids are returned gently so that the bioflocks do not break up detrimental, heavy particles, such as sand, are not returned simple structure not so easily clogged easy maintenance recycling without mixing.

BRIEF DESCRIPTION OF THE DRAWINGS

The invention will be described more fully and by way of example with reference to the accompanying drawings. In the drawings:

FIG. 1 shows a vertical cross-section of an embodiment of the invention,

FIG. 2 is a section as on the line A—A of FIG. 1, and

Figure 3:
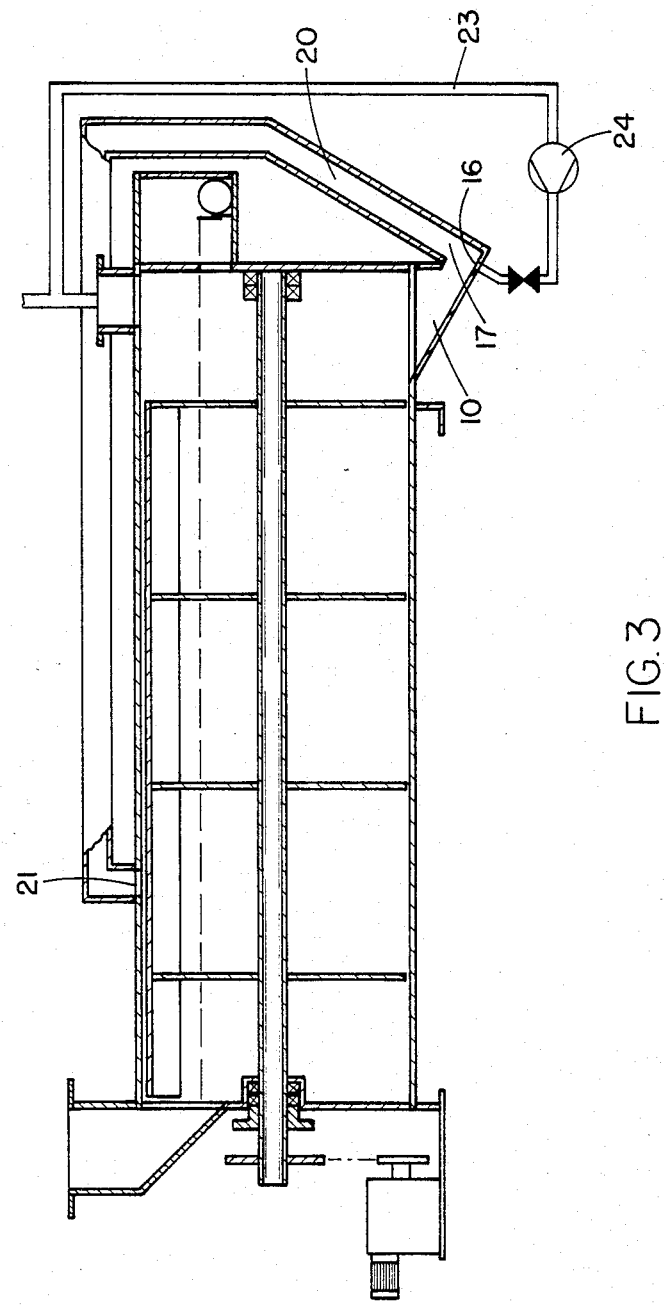
FIG. 3 shows a vertical cross-section of another embodiment of the invention.

In the figures, reference numeral 2 refers to a cylindrical jacket of a horizontal vessel 1 of the reactor. An agitator provided with mixing blades 4 rotates around a horizontal shaft 3 which is disposed inside the cylindrical jacket. The blades are connected to the shaft by round disc 25. The shaft is mounted at its both ends on bearings in the end walls 5 and 6 and connected to the power source. In the wall 5 of the vessel there is an inlet 7 for the sludge to be treated. In an opposite wall 6, there is an outlet opening 8 for the digested sludge. Additionally, the vessel is provided with at least one outlet 9 for the digestion gas, the outlet being disposed in the uppermost point of the cylindrical jacket 2 so that the outlet is connected to a gas chamber 22 disposed above the sludge surface 21. In the lowermost point of the jacket, there is a channel 10 with an inclined bottom for discharging the settled solids from the outlet end of the vessel. Furthermore, it is provided with means (not shown) for removing sand from the vessel.

The shaft 3 of the agitator is hollow. Two rows of perforations 11 and 12 are disposed in the shaft in its inlet end in an axial direction a distance apart from each other. A movable slide 13 is disposed inside the shaft, by means of which the perforations can be covered so that only the perforations of one row are open or the perforations of both rows are partly open.

At the outlet end of the reactor there is also disposed a channel 14 connecting the channel 10 with the inclined bottom and the end of the hollow shaft. In the inclined bottom 15 there are perforations 16 through which gas discharged from the outlet 9 for the digestion gas and pumped by means of a compressor 24 through a pipe 23 can be fed into the lower end of the channel 10. A mouth 17 of the channel 14 is disposed in front of the inlet openings 16 for the gas. In the channel 10 there is also a feeding screw 18 which transfers the solids to be returned to the front of the mouth of the channel 14.

The reactor operates as follows: The sludge to be digested is fed batchwise or continuously into the reactor through the inlet 7. Digested sludge settled on the bottom of the vessel and transferred through the channel 14 and the shaft 3 is added to the heated sludge. The sludge is transferred by means of gas introduced through the perforations 16. Most of the digested sludge is removed through the outlet opening 8 in the end wall 6. Pressurized gas produced in the vessel and removed through the outlet opening 9 is used as the transfer gas for the sludge returned to the inlet end of the reactor. The gas flow and thus the amount of the returned sludge is adjusted by means of a valve 19 preferably so that the operation is periodical. The sludge to be returned can be guided to a desired point in the vessel by means of the slide 13. The shaft is rotated continuously or periodically.

The alternative embodiment illustrated in FIG. 3 differs from the above presented mainly in that the digested sludge is returned from the outlet end of the reactor to the inlet end of the reactor by means of a return pipe 20 disposed outside the vessel. One end of the pipe is connected to an opening 21 in the jacket and the other end is disposed so that its mouth 17 is in front of the inlet opening 16 for the gas. The bottom of the channel 10 is so inclined that the settled solids move due to gravity in front of the inlet opening so that they can be fed to the return pipe by means of gas.

While specific embodiments of the invention have been described in detail above, it is to be understood that various modifications may be made from the specific details described without departing from the spirit and scope of the invention.

What is claimed is:

1. A reactor for anaerobic digestion of an organic sludge and for the production of methane gas, comprising an essentially horizontal, cylindrical vessel (1) having an inlet end and an outlet end, an inlet (7) for the sludge at the inlet end of the vessel, a first outlet for the digested sludge (8) at the opposite outlet end, means for stirring the sludge in the proximity of the inlet end and throughout a major portion of the vessel and extending up to the outlet end, a second outlet (9) for the removal of methane gas connected to a gas chamber in the upper portion of the vessel, means for returning the sludge settled at the bottom of the vessel at the outlet end to the inlet end, comprising a first channel (10) with an inclined bottom in the lowermost point of the vessel at the outlet end for receiving the settled sludge, said inclined bottom having perforations, a second channel (14) at the outlet end of the vessel, said means for stirring the sludge comprising a horizontal hollow perforated shaft (3) provided with blades and means for rotating said shaft, said second channel (14) fluidly connecting said first channel (10) to said perforated hollow shaft, means for discharging said gas from the second outlet (9) to said channel with an inclined bottom and said perforated shaft is provided with openings disposed a distance apart from each other in the direction of the shaft and a slide is disposed in the shaft to guide the solids to be recycled to a predetermined part of the vessel and valve means for controlling the gas flow and the amount of settled sludge which is returned to the inlet.

2. A reactor according to claim 1 wherein a feeding screw is disposed in said first channel.

* * * * *